United States Patent [19]
Kageyama et al.

[11] Patent Number: 4,971,061
[45] Date of Patent: Nov. 20, 1990

[54] APPARATUS FOR RECORDING INTRACRANIAL PRESSURE

[75] Inventors: Naoki Kageyama, Kyoto; Hiroji Kuchiwaki, 12-6 Minamigaoka 3-Chome, Nissincho, Aichi-gun, Aichi 470-01; Junki Ito, Aichi; Nobumitsu Sakuma; Yukio Ogura, both of Ibaraki; Eiji Minamiyama, Chiba, all of Japan

[73] Assignees: Hitachi Construction Machinery Co., Ltd., Tokyo; Hiroji Kuchiwaki, Aichi, both of Japan

[21] Appl. No.: 350,704

[22] PCT Filed: Sep. 25, 1987

[86] PCT No.: PCT/JP87/00704
§ 371 Date: May 11, 1989
§ 102(e) Date: May 11, 1989

[87] PCT Pub. No.: WO88/02233
PCT Pub. Date: Apr. 7, 1988

[30] Foreign Application Priority Data
Sep. 27, 1986 [JP] Japan ................. 61-227138

[51] Int. Cl.$^5$ .............................. A61B 8/02
[52] U.S. Cl. .............................. 128/660.02
[58] Field of Search ......... 128/660.02, 662.03, 128/748

[56] References Cited
U.S. PATENT DOCUMENTS
3,681,977  8/1972  Wendt et al. ............ 128/661.05

FOREIGN PATENT DOCUMENTS
55-91341   7/1980  Japan ............... 128/660.02
60-148545  8/1985  Japan ............... 128/660.02
0719610    3/1980  U.S.S.R. ............ 128/661.03
0904670    2/1982  U.S.S.R. ............ 128/660.02
1058556   12/1983  U.S.S.R. ............ 128/660.02
1142106    2/1985  U.S.S.R. ............ 128/660.02

Primary Examiner—Francis Jaworski
Attorney, Agent, or Firm—Wenderoth, Lind & Ponack

[57] ABSTRACT

An apparatus for recording the intracranial pressure of a living body or patient utilizing ultrasonic waves includes a probe which is connected to a pulser to receive intracranial echoes that are multi-reflected being interfered with each other, a receiver for amplifying the received echoes, a gate circuit which applies a gate for a predetermined time duration of echo synchronous with the heart beat among the amplified echoes and which produces internal waves of gates, and a recorder for continuously recording peak values of the output waveforms. The intracranial pressure waveforms are continuously recorded, a change in thickness of the dura mater is found from the recorded intracranial pressure waveforms and a change of the intracranial pressure is found by utilizing a correlation between the intracranial pressure and the thickness of the dura mater.

1 Claim, 9 Drawing Sheets

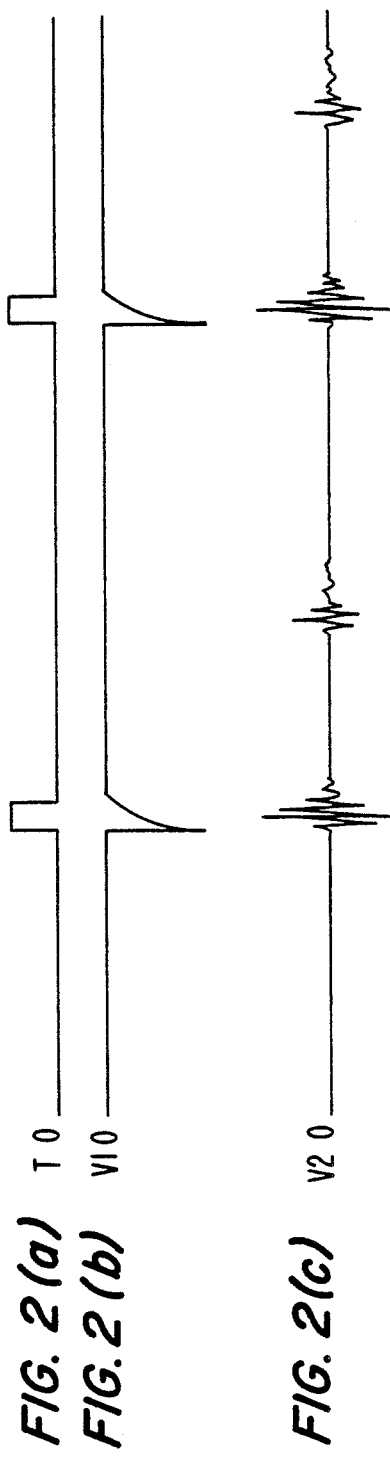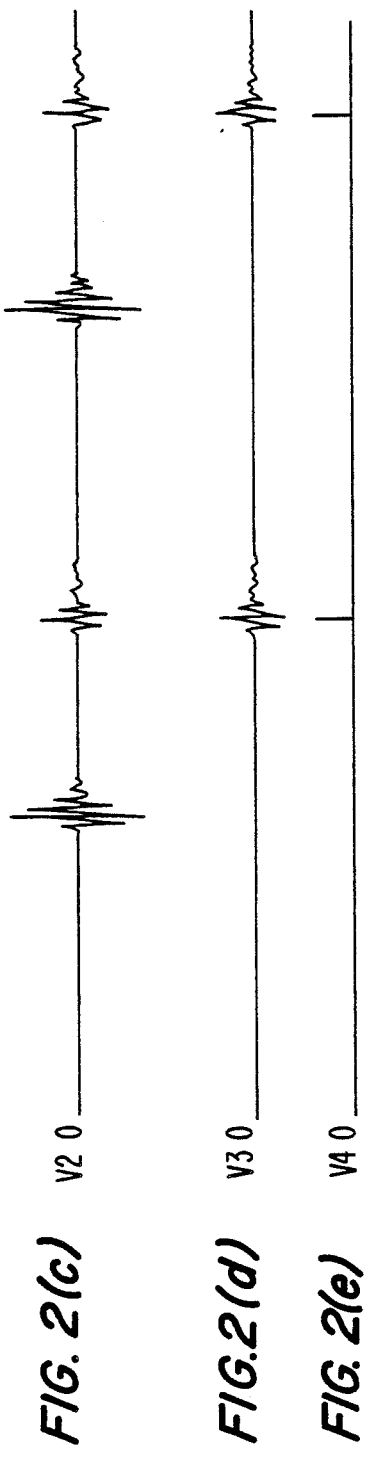
FIG. 2(a)
FIG. 2(b)
FIG. 2(c)
FIG. 2(d)
FIG. 2(e)

APPARATUS FOR RECORDING INTRACRANIAL PRESSURE

FIELD OF THE INVENTION

The present invention relates to an apparatus for recording the intracranial pressure using the ultrasound technique and more particularly to an apparatus suitably usable for recording the intracranial pressure noninvasively and safely from outside the cranium.

BACKGROUND ART

The human being in the normal condition, that is, in good health, has a constant intracranial cavity volume peculiar to himself. However, if he suffers from, for example, a lesion such as cerebral tumor, hematoma or the like or any other intracranial disease, the volume of the intracranial cavity is increased. It is said that when the increase reaches about 10% of the normal cavity volume, the intracranial pressure rises and leads to a sthenia of the intracranial pressure, whereby a variety of diseases will be caused. To make clear what these diseases and determine appropriate therapy for them, it is necessary to throw a pathologic light on the sthenia of intracranial pressure. The means and methods for such elucidation have been studied in various fields of medicine, but no satisfactory means and methods have yet been proposed. However, one of the most important means for the elucidation is the measurement of any change of the intracranial pressure (intracranial pressure waveform). Heretofore, various many methods of re the intracranial pressure have been studied and tried. Such conventional methods include, for example, the latex balloon method in which a latex balloon charged with water is introduced above the dura mater or into the cerebral ventricle inside the cranium to measure the water pressure in the balloon, thereby measuring the intracranial pressure and its waveform, and the EDP measuring method in which a part of the cranium is opened to make an osseous window through which the dura mater is exposed, a strain gauge is put into contact with the dura mater and a change of the intracranial pressure is measured as a change of strain measured by a dynamic strain gauge connected to the strain gauge. However, since the measurement of the intracranial pressure by these methods is done with an invasion to the cranium, the patient must be subject to a craniotomy and have a sensor placed inside the cranium. Thus, the conventional methods for intracranial pressure measurement have problems since the patient must bear a heavy physical and socioeconomic burdens because he has the possibility of being infected and must be in rest as hospitalized to maintain his health. In addition to the above-mentioned methods, there has been proposed a telemetry system, as a noninvasive and safe method, in which an electric resonant circuit composed of an inductance and capacitance is used of which the resonant frequency is changed by changing one of the values, inductance or capacitance, with the dislocation of a bellows or diaphragm due to the intracranial pressure and measured from above the scalp. However, this method also have practical problems; since air is used as compression medium, it, if any between the scalp and cranium, is easily affected by the temperature, the measuring gradation is required for each patient and the measuring accuracy is also far from the practical use. Heretofore, there has not yet been provided any apparatus capable of measuring the intracranial pressure easily, noninvasively without any malinfluence on the brain inside and with a high reliability, and those in the clinical fields have long waited for such apparatus.

As having been described in the foregoing, the conventional measurement of intracranial pressure has been done by the methods with an invasion to the cranium in almost all the cases while being one of the most important means in the elucidation and therapy of the intracranial pressure sthenia. There have not yet been proposed any method and apparatus which satisfy the required safety and reliability for the measurement and can make the measurement with a reduced socioeconomic burden to the patient. On the other hand, the apparatus by the noninvasive method is just under study and development, and the accuracy and costs thereof are not yet at the practical stage.

The present invention has an object to overcome the above-mentioned drawbacks of the conventional techniques by providing an apparatus capable of measuring and recording the intracranial pressure waveform from outside the cranium easily, safely, noninvasively, highly reliably and without any malinfluence on the brain inside.

DISCLOSURE OF THE INVENTION

The above object of the present invention is attained by providing an apparatus for recording the intracranial pressure, comprising a pulser which generates a voltage pulse, a probe which receives the voltage pulse from the pulser, transmits, as driven by the voltage pulse, an ultrasonic wave pulse into the cranium and receives reflection waves from inside the cranium, a receiver which amplifies the sound pressure of the reflection wave received by the probe, a gate circuit connected to the receiver and which sets a gate within a required range of the output waveform from the receiver, and a peak detector which detects peak values of the sound pressure within the gate width set by the gate circuit, and a recorder which continuously records the peak values, said probe transmitting an ultrasonic wave of which the pulse train length is more than two times larger than the thickness of the dura mater, and the gate circuit being so arranged as to set a gate to a time duration for which the interference reflection waves from the dura mater.

The above-mentioned apparatus according to the present invention utilizes the correlation that as the intracranial pressure changes, the dura mater thickness changes correspondingly, verified by the Inventors, on which any change of the intracranial pressure can be known by recording the change of the dura mater thickness.

Since the change of the dura mater thickness can be known by measuring the waveform of the intracranial pressure, the continuous recording of the intracranial pressure waveform provides for a recording of the change in thickness of the dura mater, from which the change of the intracranial pressure can be known.

For recording the above-mentioned intracranial pressure waveform, an arbitrary trigger pulse of a relatively high repetition pulse frequency (RPF) like, for example, the internal trigger inside the pulser being taken as trigger signal, a transmission pulse is sent from the pulser to the probe connected to the pulser and disposed outside the patient's cranium. In the probe, the transmission pulse sent from the pulser is converted to an ultrasonic pulse of burst wave which is transmitted into the cranium. In this case, the probe is so selected as to transmit the ultrasonic pulse of burst pulse of which the wave train length is approximately double the thickness of the intracranial thin-layer tissues such as the dura mater, arachnoid and the like. Then the ultrasonic wave transmitted into the cranium is subject to the reflections at various interstital boundaries (acoustic boundaries) such as skull, dura mater, etc., and the reflection waves interfere with each other while being subject to the transmission loss and reflection loss. The echo of the interference reflection wave is received by the probe. The received echoes also include the reflection waves from both faces of the dura mater and the interference waves resulted from the multiple reflections within the dura mater. The echo received by the probe is sent to the receiver in which it is amplified, and this amplified echo is sent to the gate circuit which receives, on the other hand, the aforementioned trigger pulse and gates the received echo sent via the above-mentioned receiver, with reference to the time duration of a predetermined echo delayed an arbitrary time from the rise of the pulse, so as to include the aforementioned interference reflection wave, thereby delivering a gated-in waveform. This output waveform is sent to a peak detector in which the peak values of the waveform are sampled and held, and are continuously recorded by the recorder.

For determining the time duration for which the above-mentioned gating is applied, it is necessary to discriminate the reflection waves from the dura mater, from those from other regions, among the echoes from inside the cranium. The echoes from inside the cranium include the reflection waves from the skull, dura mater and other portions within the cranium and the extremely complicate interference waves resulted from the mutual interference of multiple-reflection waves within the tissues of those regions. However, since the sound pressure of the reflection wave decreases rapidly as the distance from the probe to the reflecting points is longer, the echoes, among the actually received echoes, of which the sound pressure changes largely correspondingly to the heart beat can be regarded as the reflection waves from the dura mater. Therefore, even in case of an echo being an interference wave resulted from the superposition of the reflection waves from the skull and those from the dura mater, the change in sound pressure of the echo can be regarded as the change due to the thickness of the dura mater. So the gate is set within a range in which portions of echo waveform which have the sound pressure changed correspondingly to the heart beat are included.

So designed as to continuously record the intracranial pressure waveform measured from outside the cranium, the apparatus according to the present invention can make such recording easily, safely, highly reliably, noninvasively and without any malinfluence on the brain inside. The intracranial pressure waveform thus measured and recorded provides a valuable diagnostic information on the change of the intracranial pressure based on the correlation between the change in thickness of the dura mater and the change of the intracranial pressure, as will be further described with reference to the embodiment of the present invention.

BRIEF DESCRIPTION OF THE DRAWINGS

All the drawings attached are to explain the present invention, of which,

FIG. 2(a)-2(e) are operation-explanatory drawing showing the output pulses at various functional steps;

FIGS. 9 to 12 show the intracranial pressure waveforms, respectively, measured with different sthenic states of the intracranial pressure in the experiment shown in FIG. 8.

DESCRIPTION OF THE PREFERRED EMBODIMENT

Figure 1:
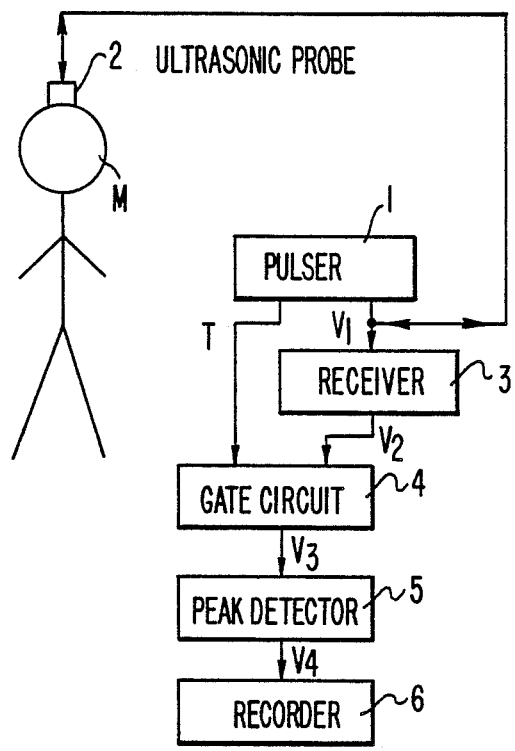
FIGS. 1 shows the system configuration of an embodiment the apparatus according to the present invention.

The embodiment of the present invention will be explained with reference to FIGS. 1 and 2(a)-2(e). FIG. 1 shows the system configuration of the apparatus according to the present invention and FIG. 2(a)-2(e) are is an operation-explanatory drawings showing the output pulses at various functional step. In Figures, the reference numeral 1 indicates a pulser connected to a probe 2 placed on the skull of the patient M and which transmits a transmission pulse V1 shown in FIG. 2 (b) to the probe 2 simultaneously with the rise of the internal trigger pulse T shown in FIG. 2 (a).

The probe 2 converts the transmission pulse V1 to an ultrasonic pulse of burst wave, that is, a pulsating wave resulting from the separation of continuous ultrasonic waves by a certain time duration, which will be transmitted into the cranium. In this case, the probe 2 is so selected as to transmit the ultrasonic pulse of burst wave of which the wave train length is approximately double the thickness of the intracranial thin-layer tissues such as dura mater, arachnoid, etc.

The ultrasonic pulse transmitted into the cranium is subject to the reflections at various interstital boundaries being the acoustic boundaries such as skull, dura mater, etc., and the reflection waves interfere with each other while being subject to the transmission loss and reflection loss. These echoes are received by the probe 2. The echoes also include the reflection waves from both faces of the dura mater and the interference waves resulted from the mutual interference of the multiple-reflection waves within the dura mater. The reference numeral 3 indicates a receiver which amplifies the echo including the interference wave received by the probe 2 and delivers an echo V2 shown in FIG. 2 (c). The reference numeral 4 indicate a gate circuit which is supplied with the echo V2 from the receiver 3 and the above-mentioned internal trigger pulse T to delay the echo V2 an arbitrary time from the rise of the pulse T as trigger signal and gate, by an arbitrary time duration, the echo V2 delivered from the receiver 3 so as to include the interference reflection wave, thereby delivering an gated-in waveform V3 as shown in FIG. 2 (d). The time duration of the echo synchronous with the above-mentioned heart beat is peculiar to each living body or patient and varies from one living body to another. Thus, the time duration is a specific one for each age, sex, etc. However, the variation is only a small one and so the small variation can be corrected by briefly adjusting the time duration.

The reference numeral 5 indicates a peak detector which supplied with a gated-in waveform V3, and samples and holds the peak values of the waveform, and then delivers the peak values V4 as shown in FIG. 2 (e). The output peak values V4 are continuously recorded by the recorder 6. The waveform defined by the peak values V4 continuously recorded by the recorder 6, that is, the intracranial pressure waveform shows the change in thickness the dura mater (the thickness including the thickness of the archnoid; this will be also true in the following) which changes correlatively correspondingly to the change of the intracranial pressure. The intracranial pressure waveform thus obtained makes it possible to know the change of the intracranial pressure and also the measurement of the intracranial pressure as the time passes provides an information of the transition of the intracranial pressure.

Thus, the measurement by the apparatus according to the present invention is not intended for measurement of the absolute value of the intracranial pressure, but utilizes the correlation between the intracranial pressure and the thickness of dura mater. So, when an information on any change in thickness of the dura mater is obtained, it is possible to know the change of the intracranial pressure.

To verify the correlation between the intracranial pressure and dura mater thickness, on which the measurement by the above-mentioned apparatus is based, the Inventors effected the following experiments on a filial grown-up dog weighing about 10 kg. An osseous window was made in the left parietal region of the dog, and a colorless transparent PVC plate was fitted in the window. The change of the state of the veins in the dura mater due to the intracranial pressure was observed and photographed. The sthenia of intracranial pressure was caused by injecting a saline into the cisterna magna to raise the intracranial pressure from 0 mmH$_2$O (before the rise of intracranial pressure) up to 700 mmH$_2$O. The observation and photography of the veins in the dura mater revealed that the veins in the dura mater appeared rather definite and showed no disturbance of the blood flow therein and that as the intracranial pressure rose, the veins in the dura mater were gradually constricted and fully constricted with no blood flow therein when the intracranial pressure reached about 600 mmH$_2$O. On the other hand, even when the intracranial pressure was lowered to less than 600 mmH$_2$O, the veins in the dura mater remained constricted. When the pressure fell down to around 200 mmH$_2$O, the blood flow was resumed in the veins. The occurrence of the constriction of the veins in the dura mater reveals that the dura mater was made thinner as compressed, and the dura mater became increasingly thinner as the intracranial pressure rose until it reached about 600 mmH$_2$O. Then the thickness of the dura mater showed no change even with the intracranial pressure further increased. It is verified from the above that there is between the intracranial pressure and the dura mater thickness a correlation that as the intracranial pressure, except for an extremely high one, rises, the dura mater becomes thinner.

The measurement according to the present invention is to get the information on the intracranial pressure by measuring the thickness of the dura mater based on the aforementioned correlation. The measurement of any change in thickness of the dura mater with the apparatus according to the present invention is done based on the theory of thin-layer reflection which will be described below. This theory will be explained with reference to FIG. 3. Take a model in which ultrasonic wave is transmitted into an assembly of a thin-layer medium 2 of acoustic impedance Z2 and thickness 1 between medium 1 of acoustic impedance Z1 and a medium 3 of acoustic impedance Z3. In Figure, r1 indicates the reflectivity when the ultrasonic wave is transmitted from the medium 1 into the medium 2, r1 indicates the reflectivity when the ultrasonic wave is transmitted from the medium 2 into the medium 3, and T1 indicates the reciprocal transmittivity when the ultrasonic wave is transmitted from the medium 1 into the medium 2. There are found beam path differences 2l, 4l, 6l, ..., 2nl between the sound pressure Pr0 of the reflection wave from the front of the medium 2 and the sound pressures Pr1, Pr2, Pr3, ..., Prn of the multiple-reflection waves within the medium, and the sound pressures are subject to a reciprocal transmission loss at the boundary B1 and reflection loss at the boundaries B1 and B2 correspondingly to the number of reflections. Assume that the wavelength of the ultrasonic wave in the medium 2 is $\Delta$ and the sound pressure of the incident ultrasonic wave is P0. Each of the above-mentioned sound pressures is expressed as follows:

$$\left. \begin{array}{l} Pr_0 = r_1 \cdot P_0 \\ Pr_1 = r_2 \cdot T_1 \cdot P_0 \cdot e^{2\frac{2\pi l}{\lambda} j} \\ Pr_2 = -r_1 \cdot r_2^2 \cdot T_1 \cdot P_0 \cdot e^{4\frac{2\pi l}{\lambda} j} \\ Pr_3 = r_1^2 \cdot r_2^3 \cdot T_1 \cdot P_0 \cdot e^{6\frac{2\pi l}{\lambda} j} \\ \cdot \\ \cdot \\ \cdot \\ Pr_n = (-r_1)^{(n-1)} \cdot r_2^n \cdot T_1 \cdot P_0 \cdot e^{2n\frac{2\pi l}{\lambda} j} \end{array} \right\} \quad (1)$$

In case the thickness l of the medium 2 is as smaller as about a half of the ultrasonic wave packet, that is, Pro, Pr1, Pro2, Pr3, ..., Prn are not separable from each other, the sound pressures will interfere with each other so that the reflection wave Pr from the medium 2 s a sum of infinite series and expressed as follows:

$$Pr = r_1 \cdot P_0 + \sum_{n=1}^{\infty} \left( (-r_1)^{(n-1)} \cdot r_2^n \cdot T_1 \cdot P_0 \cdot e^{2n\frac{2\pi l}{\lambda} j} \right) \quad (2)$$

Therefore, the reflectivity |re| at the thin-layer medium 2 can be obtained from the following equation:

$$|re| = \sqrt{1 - \frac{4\frac{Z_1}{Z_3}}{\left(\frac{Z_1}{Z_3} + 1\right)^2 \cos^2\left(\frac{2\pi l}{\lambda}\right) + \left(\frac{Z_1}{Z_2} + \frac{Z_2}{Z_3}\right) \sin^2\left(\frac{2\pi l}{\lambda}\right)}} \quad (3)$$

In case the thin-layer medium shown in Figure is included between the other two media, it is seen from the equation (3) that the reflectivity at the thin-layer medium varies periodically due to the changes in the thin-layer thickness 1 and waveform length λ and the amplitude depends upon the acoustic impedance of each medium.

Figure 3:
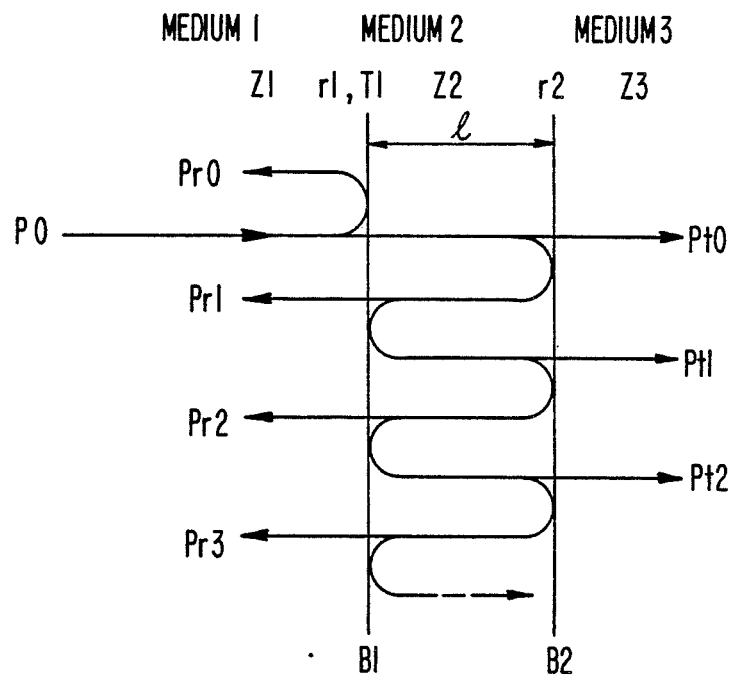
FIGS. 3 is an explanatory drawing of the theory of thin-layer reflection.

When the ultrasonic wave is transmitted from on the skull, the media, 1, 2 and 3 shown in FIG. 3 correspond to the skull, dura mater and subarchnoidal space (cerebrospinal fluid), respectively. Therefore, if the dura mater changes in thickness as the intracranial pressure changes, the echo height of the reflection wave from the boundary between the skull and dura mater also changes. Hence, by continuously measuring the echo height of the reflection wave from the boundary, the waveform of the intracranial pressure can be obtained.

Figure 4:
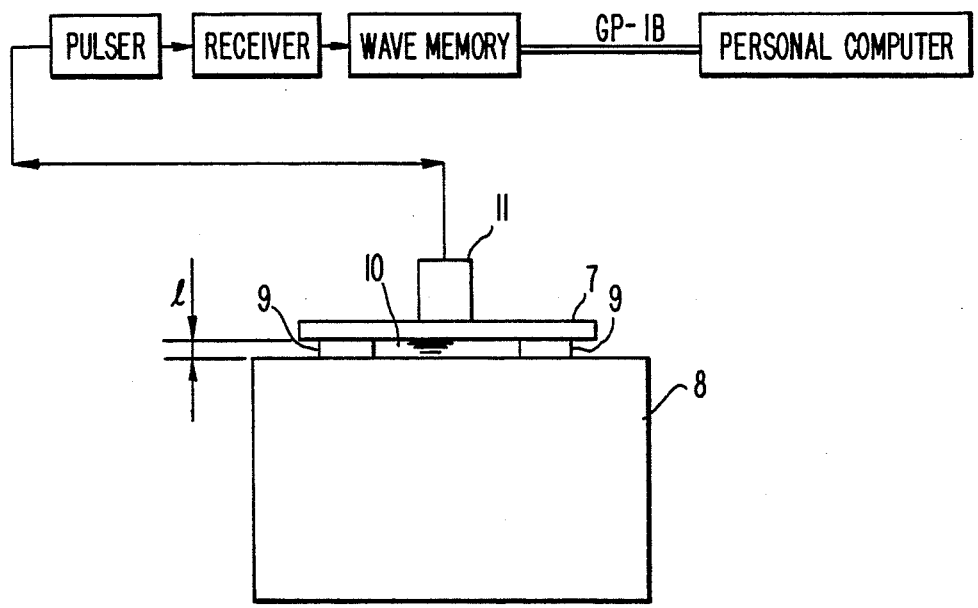
FIG. 4 is a drawing showing the experimental apparatus used for verification of the theory of thin-layer reflection and its application.

Next, for verification of the aforementioned theory of thin-layer reflection, an experiment as shown in FIG. 4 was done. Two thickness gauges 9 of a same thickness % were interposed between an acrylic plate 7 of 5 mm in thickness and a polystyrol block 8 of 50 mm in thickness, and a layer 10 of a machine oil was formed in the space defined by these elements, thereby preparing an oil layer model to prevent air from entering the space.

Figure 5:
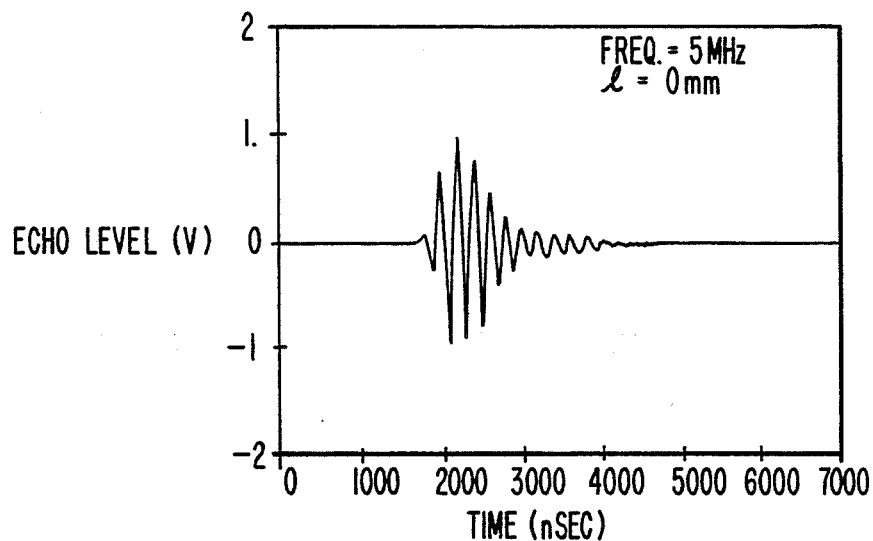
FIG. 5 is a drawing showing the reflection waveform from the bottom face of the acrylic plate in the experimental apparatus in FIG. 4.
Figure 6:
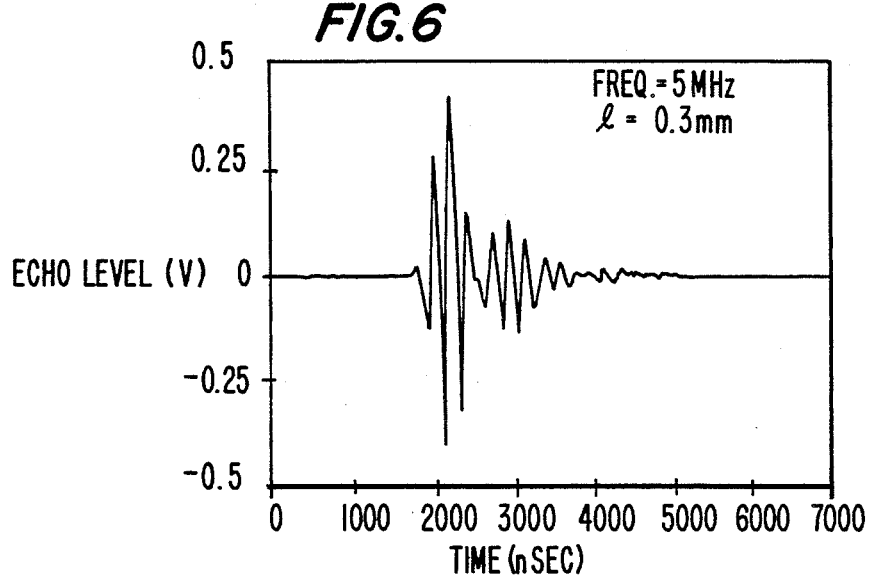
FIG. 6 is a drawing showing the reflection waveform which is the same as in FIG. 5 provided that the clearance (oil layer thickness) is 0.3 mm.

A probe 11 of a 5 MHz split type was used and it was fixed to the acrylic plate 7 using an instantaneous adhesive. FIG. 5 shows the reflection waveform (fundamental waveform) from the bottom of the acrylic plate 7, and FIG. 6 shows the reflection waveform when $l = 0.3$ mm. It is seen from these Figures that the mutual interference of the multiple-reflection waves in the oil layer causes the waveform to be deformed and the entire amplitude to be changed.

The echo height of each reflection wave was measured in the A scope with the thickness l of the thickness gauges 9 changed within a range of 0.05 to 0.5 mm and also with the oil layer thickness changed. The height of the echo from the first bottom of the acrylic plate 7 was taken as the reference echo height.

Figure 7:
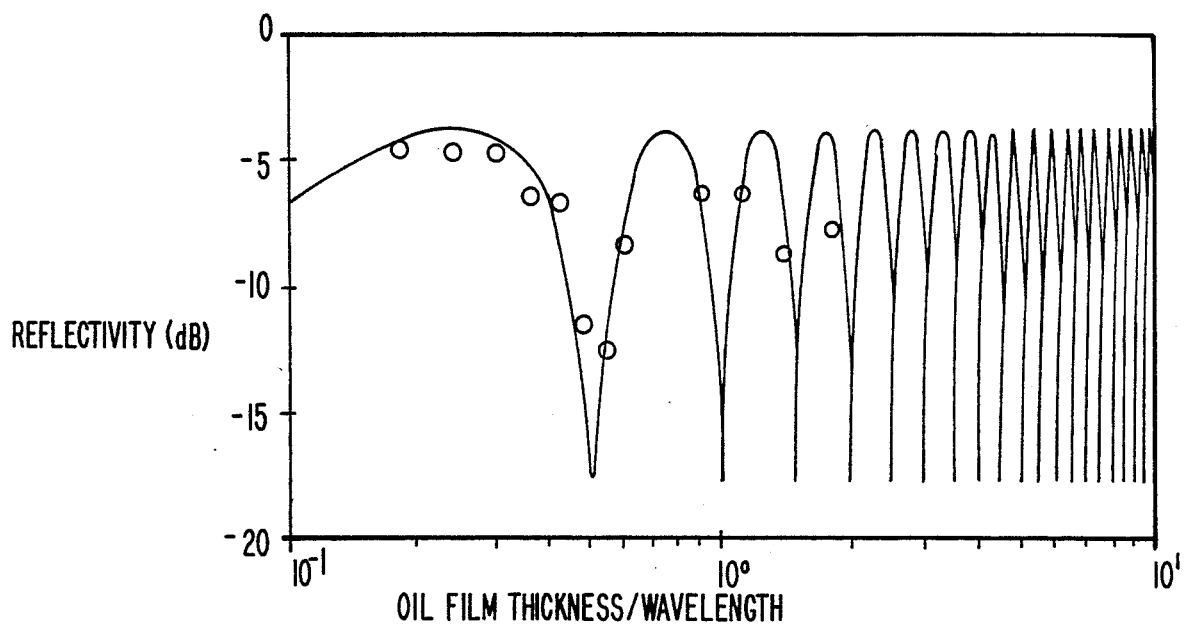
FIG. 7 is a drawing showing the comparison between the experiment results obtained with the experimental apparatus shown in FIG. 4 and the theoretical curve.

FIG. 7 shows the comparison between the experimental result and the theoretical curve obtained from the equation (3). It should be noted that the acoustic impedances of the acrylic plate 7 machine oil 10 and polystyrol block 8 were $3.21 \times 10^6$, $1.3 \times 10^6$ and $2.46 \times 10^6$ kg/cm² sec, respectively and that the acoustic velocity of the machine oil 10 was taken as 1,400 m/sec. They were found very similar to each other, which verified that the theory of thin-layer reflection has not any problem in practice.

As seen from FIG. 7, the interference wave due to the multiple reflections at the dura mater has a portion of which the reflectivity changes greatly even when the thickness changes only a little. The experimental measured values shown as encircled in FIG. 7 were obtained with the thickness of the oil layer changed in a wide range (the maximum value of the thickness is 10 times of the minimum value) but the change of the dura mater of a living body is actually less than 20% when the intracranial pressure changes. This range of change is fully included in the range between one peak and valley of many waveforms appearing in the reflectivity diagram of the interference wave shown in FIG. 7. Even with a slight change in the dura mater, the reflection wave from the dura mater is an interference wave as in the above, so its sound pressure will change largely. Therefore, the change of the intracranial pressure can be observed as a clear change in sound pressure of the ultrasonic echo. When the change in thickness of the dura mater just falls on the peak or valley of the waveform in FIG. 7, the change in the echo sound pressure corresponding to the change in thickness of the dura mater is indefinite. To avoid this, the output frequency of the pulser is changed so that the change in sound pressure of the reflection wave appears clearly.

Next, the following experiments were done with the dog in order to review whether or not the verification done with the aforementioned apparatus is applicable to a living body or patient.

The experiments were done with a filial grown-up dog weighing about 10 kg. First, 5 to 6 ml of 2% (weight per volume) hydrochloric acid morphine was injected into the muscle of the dog for the basal anesthesia. Thereafter, 100 to 150 mg of thiamylal sodium was administered to the dog by intravenous injection for insufflation anesthesia, and the dog was placed in prone position under an endotracheal tube with the head immobilized on the Tohdai-Nohken stereotaxic table for use with dogs (this table was developed by the Tohdai-Nohken = the Brain Research Institute of Tokyo University). Thereafter, 10 to 15 mg of thiamylal sodium was additionally administered to the dog at every about 60 minutes for maintenance anesthesia as necessary and thus the experiment was done while the dog was keeping the spontaneous natural breathing.

Figure 8:
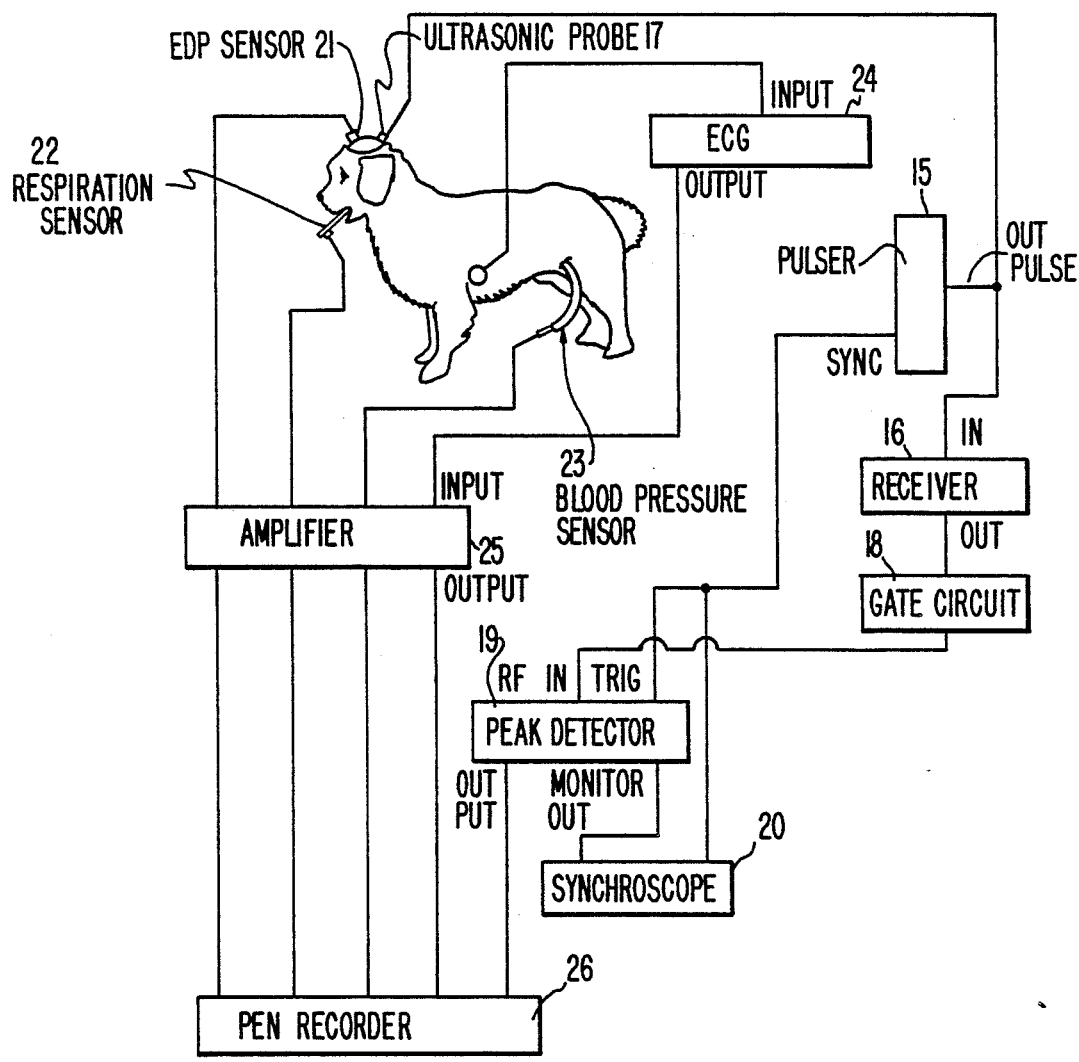
FIG. 8 is a block diagram of the experimental apparatus used in a test on a dog.

The block diagram of the experimental system is shown in FIG. 8. In the Figure, the reference numeral 15 indicates pulser, 16 a receiver which receives and sends an electric signal with respect to an ultrasonic probe 17, 18 a gate circuit which gates the received waveform with an arbitrary delay time duration to provide a gated-in waveform, 19 a peak detector to sample and hold the maximum value of the gated-in waveform, 20 a synchroscope to monitor the received waveform, 21 is an EDP sensor which transduces the intracranial pressure measured outside the dura mater into an electric signal, 22 a respiration sensor which picks up the respiration as a change of temperature and transduces the respiration change into an electric signal, 23 a blood pressure sensor intended for monitoring the systemic blood pressure and which transduces the blood pressure into an electric signal, 24 an ECG (electrocardiograph) which delivers an ECG (electrocardiogram) waveform and generates a trigger signal as delayed an arbitrary time from the R-wave of the ECG waveform, 25 an amplifier which amplifies the signals sent from the EDP sensor 21, respiration sensor 22, blood pressure sensor 23 and ECG 24, and 26 a pen recorder which continuously records the ECG waveform, respiration waveform, systemic blood pressure waveform, intracranial pressure waveform (output of the EDP sensor) and the intracranial pressure waveform (output of the peak detector) obtained by the ultrasonic technique.

In the experiments, the intracranial pressure detected by the EDP sensor, systemic blood pressure, ECG and respiration were monitored bsesides the intracranial pressure measured with the ultrasonic technique. For measurement of the intracranial pressure by the EDP sensor 21, the EDP sensor 21 was attached on the right side of the dog's head and the extradural pressure was measured. The systemic blood pressure was measured with a catheter of 2 mm in inside diameter and about 400 mm in length inserted from the femoral artery and self-retained in the thoracic aorta and by a catheter-tip type pressure gauge. The ECG was measured by the ECG (electrocardiogram) having the electrodes thereof attached on the four extremities, respectively, of the dog. The respiration was measured using a thermistor probe attached to the tip of the endotracheal tube.

The experiments using the ultrasonic technique were conducted as follows:

As shown in FIG. 8, the trigger switch of the pulser 15 was changed over to the internal trigger, and the entire system was started with the internal trigger of the pulser 15. The trigger pulse interval was 85.2 sec, namely, the pulse repetition frequency (PRF) was 11.4 kHz.

A probe 17 of 5 MHz split-type was used to gate the reflection waveform from the boundary between the skull and dura mater, and the maximum value of the gated-in waveform was measured by the peak detector 19. The result of the measurement was recorded by the pen recorder 26 simultaneously with the ECG, respiration waveform, systemic blood pressure waveform and the intracranial pressure waveform obtained by the EDP sensor 21.

The intracranial pressure sthenia models used were the following three:

(1) Group with injection of saline into the cisterna magna:
  An 18-gauge metallic needle was punctured into the cisterna magna and saline was injected to apply a hydrostatic pressure, thereby raising the intracranial pressure.
(2) Group with inhalation of $CO_2$ gas:
  $CO_2$ gas produced from dry ice by evaporation was inhaled through an endotracheal tube to raise the intracranial pressure.
(3) Group with cervical compression:
  The cervical compression was artificially made to cause an intracranial pressure rise due to the phlenostasis.

Figure 9:
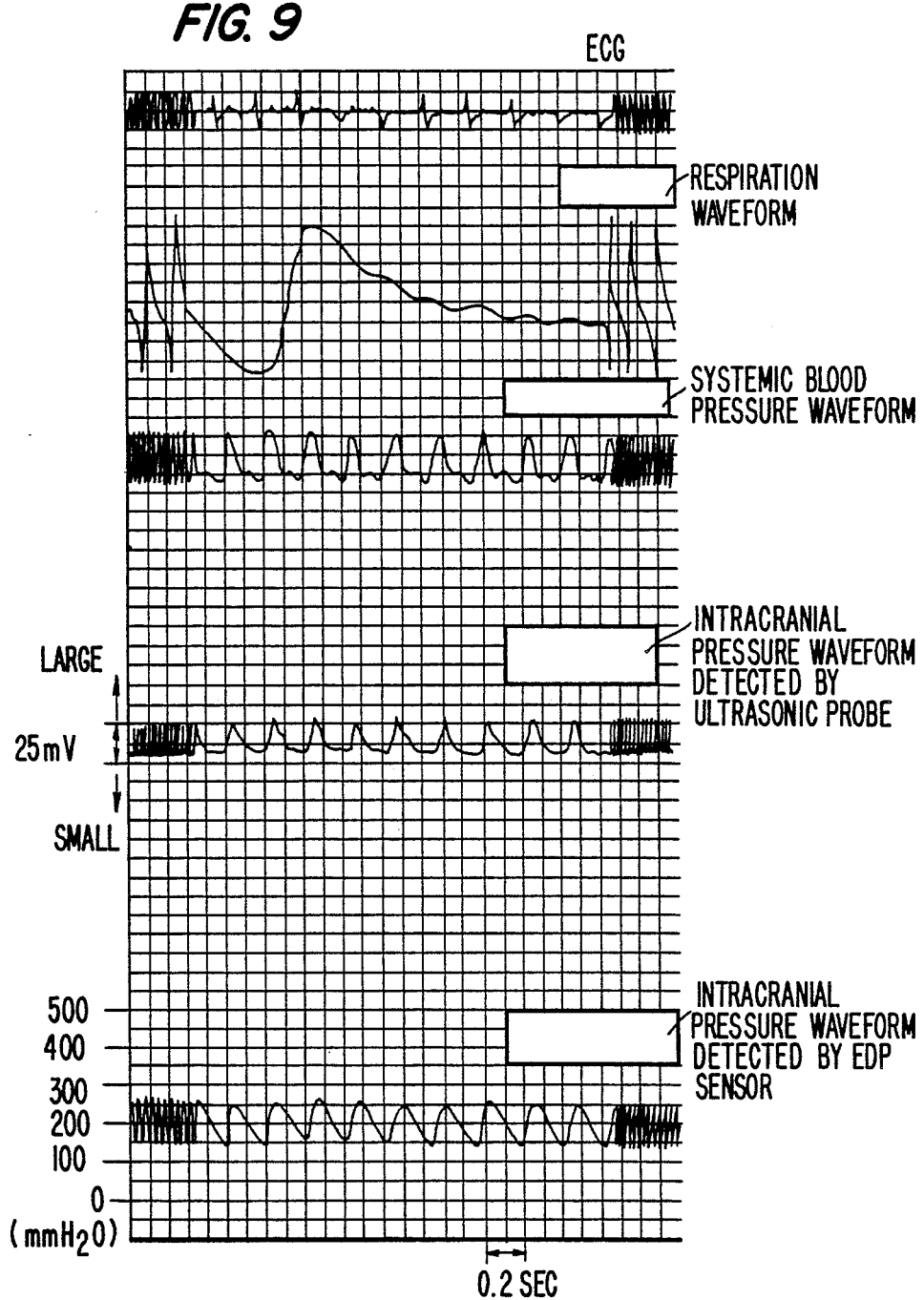
FIG. 9 is a drawing showing a pattern of the intracranial pressure waveform before the sthenia of the intracranial pressure.

The pattern of the intracranial pressure waveform obtained by the ultrasonic technique is shown in FIG. 9. The ultrasonic probe 17 used was of a 5 MHz split type, and the measurement was done from on the skull.

FIG. 9 shows the following:

(1) The ECG, systemic blood pressure waveform and EDP sensor-measured intracranial pressure waveform are pulsated synchronously with the intracranial pressure waveform measured by the ultrasonic technique.
(2) The intracranial pressure waveform measured by the ultrasonic technique shows a similar shape to the systemic blood pressure waveform, and the peak positions are coincident with those of the intracranial pressure waveforms measured by the EDP sensor.
(3) The peak of the systemic blood pressure waveform appears as delayed about 70 msec from the peak of the ECG, and the peaks of the intracranial pressure waveforms measured by the ultrasonic technique and EDP sensor, respectively, appear as delayed a further 10 msec.

The intracranial pressure sthenia models were (1) the group with injection of saline into the cisterna magna, (2) the group with inhalation of $CO_2$ gas, and (3) the group with cervical compression as mentioned above, but since they are different in mechanism from each other, they are also different in change pattern of the intracranial pressure pattern each other.

The results of the experiments with these models will be described below.

Figure 10:
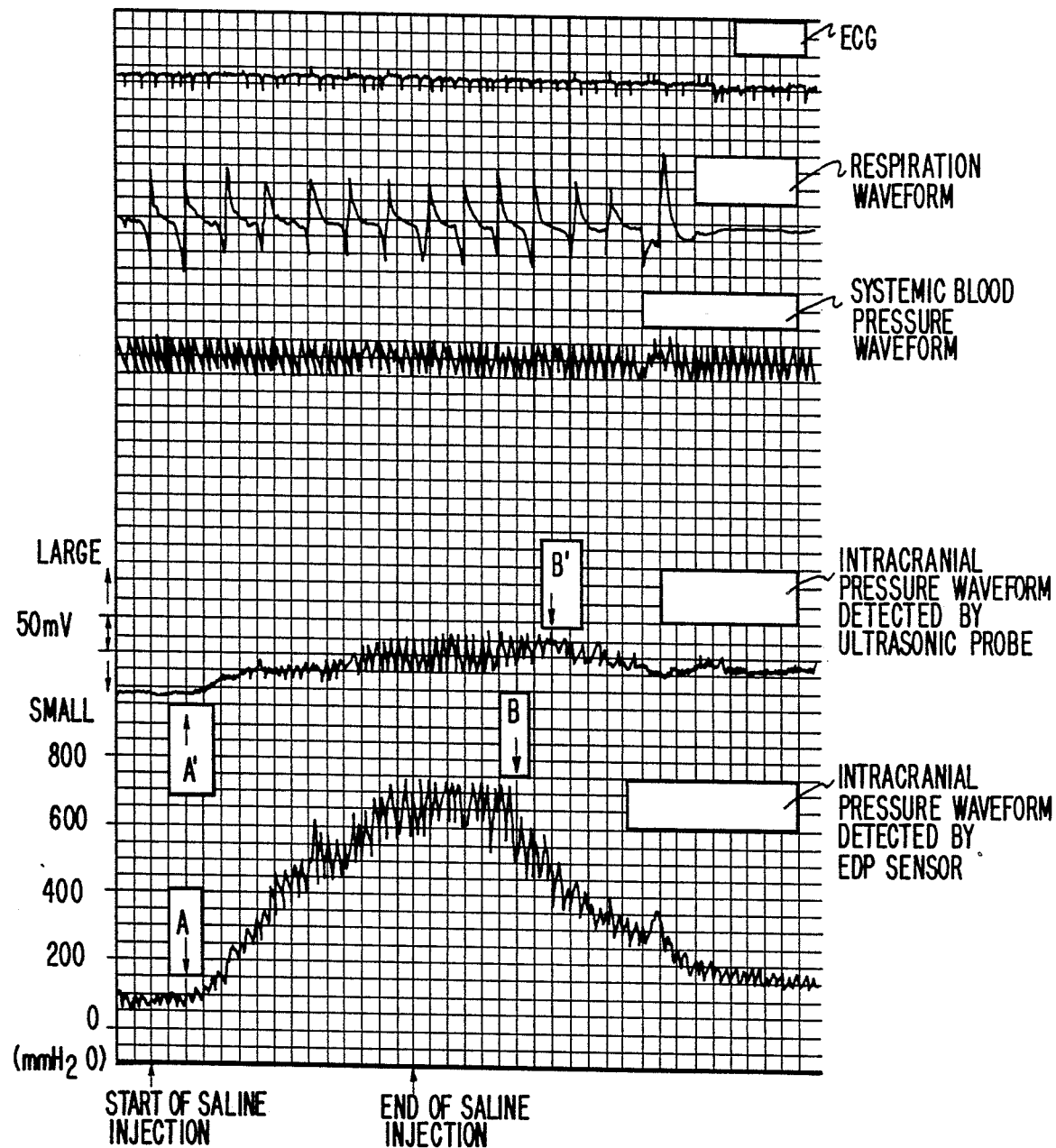

(1) Group with injection of saline into the cisterna magna:
The example of the results of the intracranial pressure waveform measurement with the group with injection of saline into the cisterna magna is shown in FIG. 10. The EDP sensor-measured intracranial pressure waveform rises gently initially after the start of the injection and then abruptly (as seen at the point A), and after the injection is completed, the maximum level is maintained for a while, followed by a rapid fall from the point B. The amplitude of the waveform becomes larger as the pressure rises.

Figure 11:
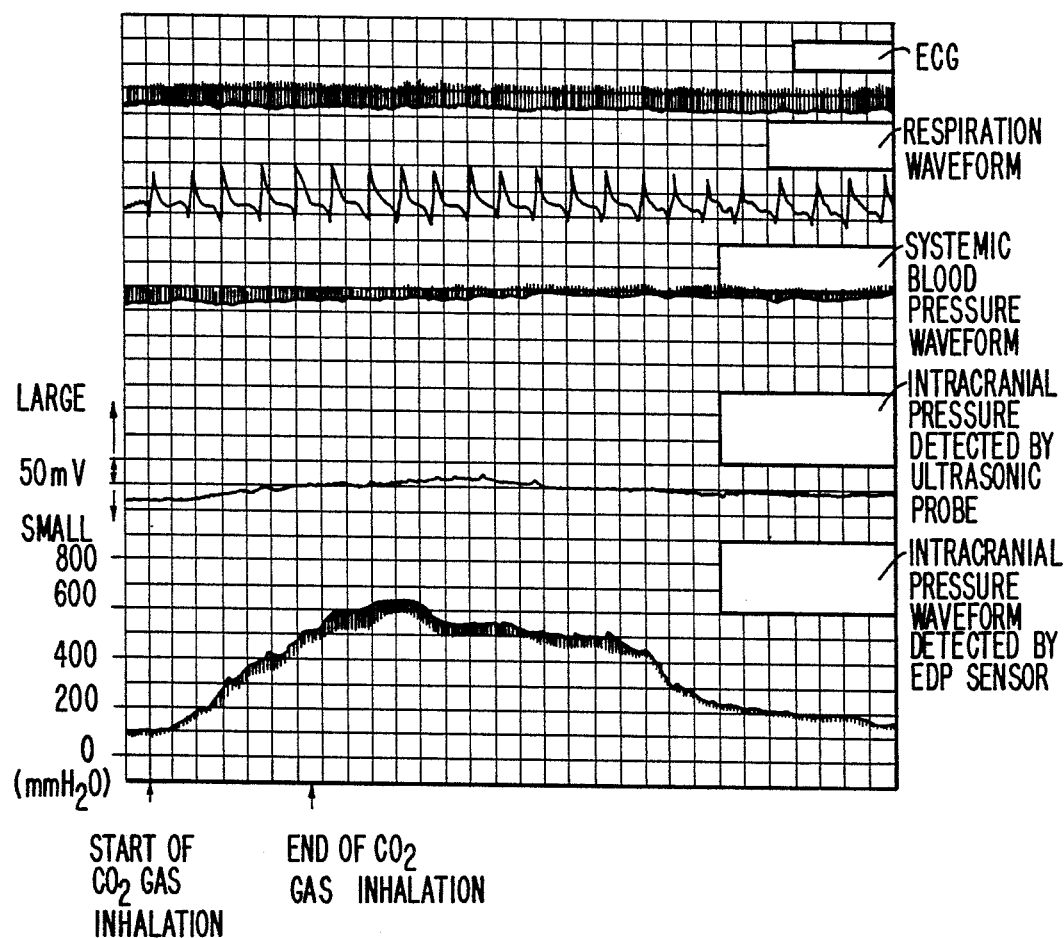

The intracranial pressure waveform measured by the ultrasound shows no larger change, but after the injection is started, it starts an abrupt rise at the point A' as in the case of the EDP sensor-measured intracranial pressure waveform. After the maximum level is maintained after the injection is completed, the waveform falls from the point B delayed from the point B. The amplitude varies following up with the change of the pressure, well corresponding to the amplitude change of the EDP sensor-measured intracranial pressure waveform (2) Group with inhalation of $CO_2$ gas:
The example of the results of intracranial pressure measurement with the group with inhalation of $CO_2$ gas is shown in FIG. 11.

After the inhalation of $CO_2$ gas is started, the EDP sensor-measured intracranial pressure waveform gently rises, and after it continues rising also after the inhalation is completed, it falls gently. The amplitude of the waveform becomes large and small as the pressure rises and falls as in the case of the group with injection of saline into the cisterna magna.

Similarly to the EDP sensor-measured intracranial pressure waveform, the intracranial pressure waveform measured by the ultrasonic technique rises gently after the inhalation of $CO_2$ gas is started, and it continues rising also after the inhalation is completed until it reaches the peak value. Then, it falls very gently and returns to the initial level. The amplitude corresponds very well in change to the amplitude of the EDP sensor-measured intracranial pressure waveform.

Figure 12:
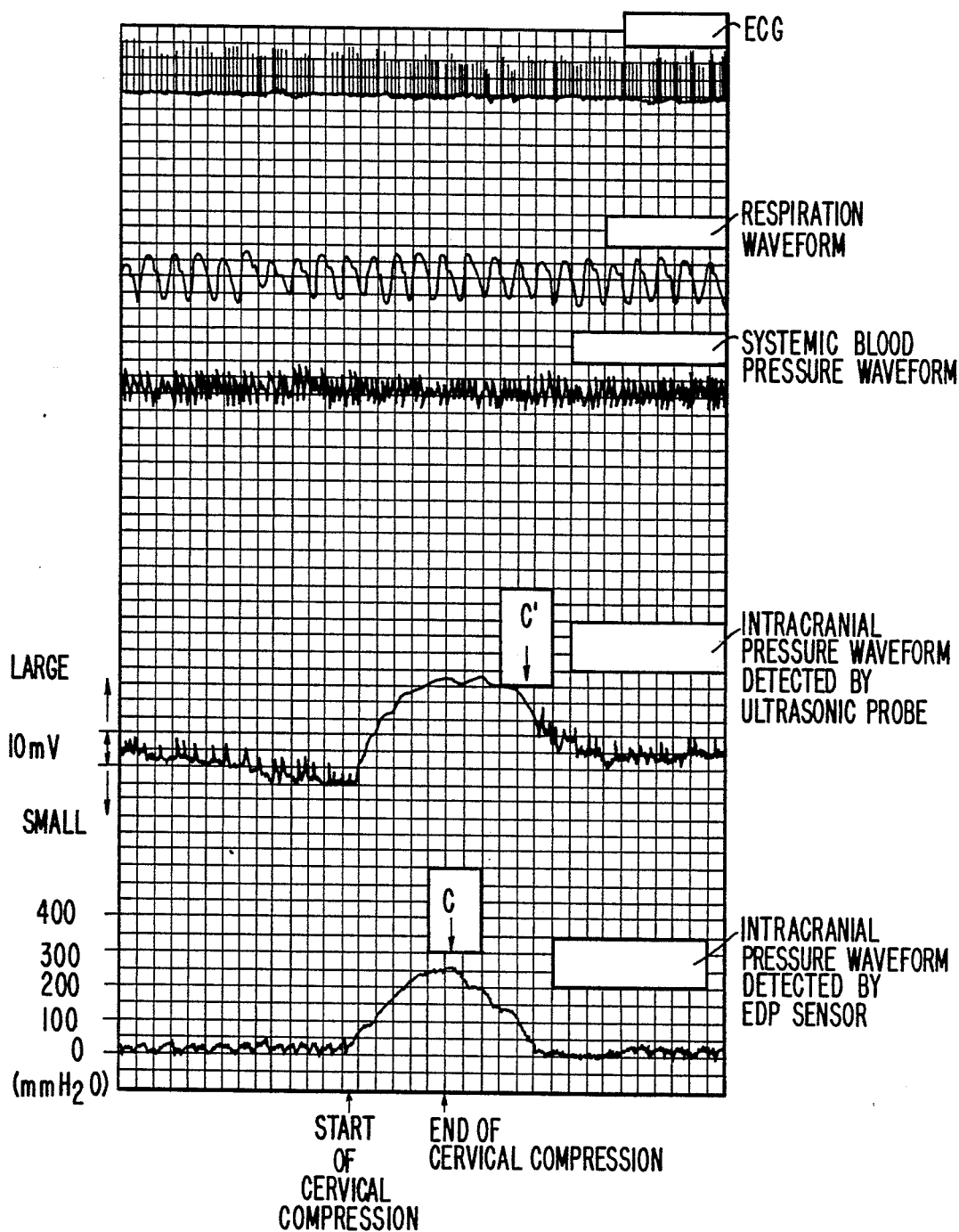

(3) Group with cervical compression:
The sample of the intracranial pressure measurement results with the group with cervical compression is shown in FIG. 12.

As the compression is increased after the cervical compression is started, the EDP sensor-measured intracranial pressure waveform rises sharply. When the compression is weakened, the waveform falls correspondingly. The amplitude is smaller while the pressure is increased. In this respect, the group with cervical compression is different from the former two groups.

The intracranial pressure waveform measured by the ultrasonic technique rises abruptly upon start of the compression and reaches the maximum level. Even when the compression is weakened, the waveform keeps the maximum level for a while, and starts falling from the point C' delayed from the point C at which the EDP sensor-measured intracranial pressure waveform starts falling. Similarly to the EDP sensor-measured intracranial pressure waveform, the amplitude becomes small as the pressure rises. The amplitude changes more noticeably than the intracranial pressure waveform measured by the EDP sensor.

The results of the measurements with the above-mentioned three models of intracranial pressure sthenia can be summed up as follows:

(I) The change in amplitude of the ultrasound-measured intracranial pressure waveform well corresponds to the amplitude of the EPD sensor-measured intracranial pressure waveform.

(II) When the intracranial pressure rises, the ultrasound-measured intracranial pressure waveform changes well correspondingly to the change of the EDP sensor-measured intracranial pressure waveform.

(III) In case the pressure changes slowly when the intracranial pressure falls, as in the group with inhalation of $CO_2$ gas, the ultrasound-measured intracranial pressure waveform well corresponds to the EDP sensor-measured intracranial pressure waveform, but in case the pressure changes abruptly as in the groups with injection of saline into the cisterna magna and cervical compression, the intracranial pressure waveform measured by the ultrasonic technique shows a time lag and so changes as delayed from the point at which the intracranial pressure waveform measured by the EDP sensor starts falling.

The phenomena shown as in (II) and (III) can be explained by the following fact that when a pressure applied to the skin is suddenly removed, the skin will not restore its initial state, and they well correspond to a phenomenon that the dura mater restored its normal thickness faster only when the basic value of the intracranial pressure fell down to about 200 mmH$_2$O, for the reason that since when the dura mater is applied with a pressure, it will be thinner without any time lag under the pressure, but when the pressure is abruptly reduced, the dura mater will not recover its thickness following up with the change of the pressure, as in the previously mentioned constriction experiment on the intradural veins.

With the acoustic impedances of the skull and dura mater and the acoustic velocity and basic thickness of the dura mater being different, the relationship between the dura mater thickness and the echo height of reflection wave is different. These parameters (more particularly, the acoustic impedance) are different from one living body or patient to another. Therefore, it is difficult to quantitatively measure and record the intracranial pressure by the apparatus according to the present invention, but it is possible to estimate the state of the intracranial pressure by analysis of the waveform patterns as shown in FIGS. 9 to 12.

In the foregoing, the measurements of intracranial pressure of a grown-up dog by the apparatus according to the present invention have been described. When such measurement is applied to a human body, it is necessary to taken in consideration the differences in shape and size of his cranium and encephalomeninges from the dog's. Concerning, for example, the skull, both the dog's cranial volume and curvature are small and the irregularities on the inner wall are large, but the cranial volume and curvature of the human being's skull are both large and the irregularities on the inner wall are extremely small. Thus, the probe can be easily attached on the human being's skull and the ultrasound wave can be smoothly transmitted and reflected. Also, the dog's dura mater thickness is about 0.2 mm while the human being's dura mater thickness is about 1.0 mm, which means that the change of human being's dura mater thickness due to the change of the intracranial pressure will be about 5 times larger than that of the dog under the assumption that the change occurs at a same rate, which suggests that the intracranial pressure of human being can be measured with a correspondingly higher accuracy, for the intracranial pressure is measured and recorded by the apparatus according to the invention utilizing the correlation between the change of dura matter thickness and the intracranial pressure.

By the way, any measuring/recording apparatus intended for use with the human being must be quite safe without any danger. For the apparatus according to the present invention, it must be proved that the ultrasound transmitted into the cranial when measuring and recording the intracranial pressure does not adversely affect the cranium itself and the human body. For this issue, the following report has been publicized. It reads as follows. Namely, concerning the influence of the ultrasound on the chromsomes, it was provided that the irradiation of an ultrasound of 500 mW/cm$^2$ in mean output and 50 W/cm$^2$ in peak output to the human peripheral lymphatic corpuscles in the premitotic period for 60 minutes shows no influence on the lymphatic corpuscles. Also, it was proved that an ultrasound of about 600 mW/cm$^2$ at maximum in mean output has no danger to the flowing red blood corpuscles, growth of cultured cells, and embryo or fetus. The mean output of the ultrasound used in the embodiment of the present invention is about 0.1 mW/cm$^2$, and so has no influence on the human body. Therefore, it can be said that the apparatus according to the present invention has no problem as to the safety to the human body.

As having been described in the foregoing, the apparatus according to the present invention is so designed as to transmit an ultrasound or ultrasonic wave from a probe into a living body or patient from outside the cranium and continuously record the echoes of interference reflection wave derived from the multiple reflections inside the cranium, for which the change of dura mater thickness can be determined from the recorded intracranial pressure waveforms, thereby obtaining the change of the intracranial pressure from the correlation between the intracranial pressure and the dura mater thickness. Thus, the apparatus according to the present invention can measure and record the change of intracranial pressure easily, safely, noninvasively, highly reliably and without any adverse affect on the brain inside. Furthermore, by periodically effecting such recording by the apparatus according to the present invention, a highly reliable diagnostic information on the pathology and a lesion-preventive information can be provided.

What is claimed is:

1. An apparatus for recording peak values of the sound pressure of reflected ultrasonic waves which correspond to an intracranial pressure of a patient, comprising:

a pulser for generating a voltage pulse;

a probe for receiving said voltage pulse from said pulser and for transmitting an ultrasonic wave pulse into a cranium of the patient and for receiving reflected ultrasonic waves from inside of said cranium, said ultrasonic wave pulse being transmitted in accordance with said voltage pulse;

a receiver connected to said pulser for amplifying the sound pressure of said reflected ultrasonic waves received by said probe and for providing output waveforms corresponding thereto;

a gate circuit, connected to said receiver, for setting a gate within a required range of said output waveforms from said receiver;

a peak detector connected to an output of said gate circuit, for detecting peak values of the sound pressure within the gate width set by said gate circuit by detecting peak values of said output waveforms from said receiver as gated by said gate circuit; and a recorder for continuously recording said detected peak values;

wherein said probe transmits an ultrasonic wave having a pulse train length which is more than twice as large as a thickness of dura mater inside said cranium, and wherein said gate circuit is so arranged as to set its gate to a time duration corresponding to the time in which reflection waves from said dura mater occur.

* * * * *